United States Patent
Benford

(10) Patent No.: US 11,219,389 B2
(45) Date of Patent: Jan. 11, 2022

(54) GAIT ANALYSIS AND ALERTING SYSTEM

(71) Applicant: Jacob Benford, Aptos, CA (US)

(72) Inventor: Jacob Benford, Aptos, CA (US)

( * ) Notice: Subject to any disclaimer, the term of this patent is extended or adjusted under 35 U.S.C. 154(b) by 687 days.

(21) Appl. No.: 15/813,802

(22) Filed: Nov. 15, 2017

(65) Prior Publication Data

US 2018/0132758 A1 May 17, 2018

Related U.S. Application Data

(60) Provisional application No. 62/422,472, filed on Nov. 15, 2016.

(51) Int. Cl.
*A61B 5/11* (2006.01)
*A61B 5/103* (2006.01)
(Continued)

(52) U.S. Cl.
CPC ............ *A61B 5/112* (2013.01); *A43B 3/0005* (2013.01); *A61B 5/1038* (2013.01);
(Continued)

(58) Field of Classification Search
CPC ... A61B 5/6802; A61B 5/6807; A61B 5/1038; A61B 5/1118; A61B 2562/0247; A61B 2562/0219; A61B 5/113; A61B 5/1115; A61B 5/1114; A61B 5/1116; A61B 5/1117; A61B 2503/10; A61B 5/112; A61B 5/1036; A61B 5/1122; A61B 5/0022; A61B 5/742; A61B 5/746; A43B 1/0054; A63B 24/0062; A63B 24/0021; A63B 2220/836;
(Continued)

(56) References Cited

U.S. PATENT DOCUMENTS

| 5,885,229 | A  | * | 3/1999 | Yamato ................ | A61B 5/1038 600/587 |
| 7,756,722 | B2 | * | 7/2010 | Levine ................. | G06F 19/3418 705/2 |
| 8,738,321 | B2 | * | 5/2014 | Yuen .................... | A61B 5/6838 702/160 |
| 9,360,343 | B2 | * | 6/2016 | Stevens ................. | A61B 5/112 |

(Continued)

FOREIGN PATENT DOCUMENTS

WO WO-2015164456 A2 * 10/2015 ......... G06F 19/3481

OTHER PUBLICATIONS

"F-Scan® In-Sole Analysis System" by Tekscan (Feb. 2, 2015) [Downloaded Jan. 31, 2020] (Year: 2015).*

*Primary Examiner* — David J. McCrosky
(74) *Attorney, Agent, or Firm* — Donald R. Boys; Central Coast Patent Agency LLC

(57) ABSTRACT

A system has pressure sensors integrated with a first article of footwear worn by a test subject on a left foot, pressure sensors integrated with a second article of footwear, worn by a test subject on a right foot, positioning circuitry determining separation and direction of the first article of footwear relative to the second article of footwear, circuitry collecting readings from the first and second plurality of sensors, and from the positioning circuitry, as variables with respect to time, and communicating the readings to a computerized diagnostic apparatus. The computerized diagnostic apparatus processes the readings for a test period of time, determining gait characteristics for the test subject, including at least stride length and timing, and width of stance, and records the gait characteristics, time and date stamped, in a manner to be retrieved and displayed.

14 Claims, 9 Drawing Sheets

(51) Int. Cl.
*A43B 3/00* (2006.01)
*A61B 5/00* (2006.01)

(52) U.S. Cl.
CPC .......... *A61B 5/6802* (2013.01); *A61B 5/0022* (2013.01); *A61B 5/742* (2013.01); *A61B 5/746* (2013.01); *A61B 2503/10* (2013.01)

(58) Field of Classification Search
CPC ............ A63B 2220/40; A63B 2220/56; A63B 2225/50; A63B 2024/0025; A63B 2225/54; A63B 2024/0071; A63B 2220/12; A63B 2220/13; A63B 2220/20; A63B 2220/58; A63B 2220/51; A63B 2220/16; A63B 2220/803; G16H 40/63
USPC ....................................................... 600/592
See application file for complete search history.

(56) References Cited

U.S. PATENT DOCUMENTS

| | | | |
|---|---|---|---|
| 2006/0143645 A1* | 6/2006 | Vock | A43B 3/0005 725/9 |
| 2008/0292179 A1* | 11/2008 | Busch | A43B 17/00 382/154 |
| 2009/0079559 A1* | 3/2009 | Dishongh | A61B 5/1113 340/539.13 |
| 2010/0198111 A1* | 8/2010 | Milani | A43B 3/0005 600/592 |
| 2013/0211290 A1* | 8/2013 | Lee | A43B 3/0005 600/592 |
| 2015/0065920 A1* | 3/2015 | Hsieh | A61B 5/0002 600/592 |
| 2017/0238845 A1* | 8/2017 | Wei | A61B 5/6828 |
| 2018/0070877 A1* | 3/2018 | Tian | A43B 17/00 |

* cited by examiner

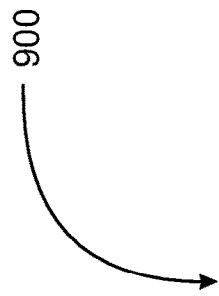

| Client Identification - name, address, email, telephone, Facebook URL, for example. |
| Categorization - senior, disabled, athlete, metalworker, fireman, policeman, for example |
| Affiliation - NBA, Pacers, NFL, Bulls, resident Safeplace Nursing Center, for example |
| Test History - Test types, date and time, number of repetitions, links to actual data |
| Test Scheduling - Test types, date and time, number of repetitions |
| Current primary focus - monitor for concussion and recovery, for example |
| DATA |

*Fig. 9*

GAIT ANALYSIS AND ALERTING SYSTEM

CROSS-REFERENCE TO RELATED APPLICATIONS

The present case claims priority to a provisional patent application, Ser. No. 62/422,472 filed Nov. 15, 2016, and all disclosure of the parent application is incorporated herein at least by reference.

BACKGROUND OF THE INVENTION

1. Field of the Invention

The present invention is in the field of human gait analysis and use of resulting information, and pertains particularly to methods and apparatus for discerning gait characteristics and applying knowledge acquired to current issues revolving treatment or diagnosis.

2. Discussion of the State of the Art

Systems are known in the art that employ sensors in wearable items for a purpose of measuring, recording, and then analyzing human movement, as recorded by the sensors. Recorded movements may be interpreted relative to diagnostic issues in medicine or relative to ongoing treatment of sports injuries and other conditions.

In systems known to the inventor, sensors might be placed within shoes or stockings to sense gait characteristics. Usually tests using such equipment are performed by a doctor or experienced practitioner when the subject of the testing is in a facility where such equipment is available and understood by the doctor or practitioner. A limitation of gait analysis under these controlled conditions is that there is an artificial environment, and a subject's behavior may be altered accordingly. A subject under these conditions may be too conscious of his or her performance.

Conventional systems have other drawbacks, as well, such as a limited consideration of characteristics of movement that might otherwise be important to diagnosis of conditions that may be apparent from gait analysis.

Therefore, what is clearly needed is a gait analysis and alert system that is fully automated and mobile, and that is enabled to consider data from a wide variety of measurements, and also capable of associating gait characteristics with a broad variety of conditions or developing conditions, and capable of a range of alerts.

BRIEF SUMMARY OF THE INVENTION

In an embodiment of the invention a system for diagnosis is provided, comprising a first plurality of pressure sensors integrated with a first article of footwear, the first article of footwear worn by a test subject on a left foot, a second plurality of pressure sensors integrated with a second article of footwear, the second article of footwear worn by a test subject on a right foot, positioning circuitry communicating between the first article of footwear and the second article of footwear, determining separation and direction of the first article of footwear relative to the second article of footwear, and circuitry collecting readings from the first and second plurality of sensors, and from the positioning circuitry, as variables with respect to time, and communicating the readings to a computerized diagnostic apparatus. The computerized diagnostic apparatus processes the readings for a test period of time, determining gait characteristics for the test subject, including at least stride length and timing, and width of stance, and records the gait characteristics, time and date stamped, in a manner to be retrieved and displayed.

In one embodiment of the system the recorded gait characteristics are recorded associated with a test identification tag, and stored associated with the test subject, creating a chronological record of multiple tests for the same subject. Also in one embodiment, gait characteristics for a test for the test subject are compared with gait characteristics for the same subject in a previous test, and differences are considered in diagnostic determination. Also in one embodiment the system further comprises a network-connected domain maintaining and updating gait characteristics for a plurality of test subjects, each test subject having a data profile wherein test results are stored chronologically, the network-connected domain executing software, providing access to the data to registered practitioners for diagnostic purposes.

In one embodiment of the system the first plurality of pressure sensors is arranged in an areal fashion relative to the sole of the first article of footwear, and the second plurality of sensors is arranged in an areal fashion relative to the sole of the second article of footwear, providing pressure distribution readings from the sensors relative to time, such that timing for pressure application at distinct portions of the sole of the test subject's foot are recorded relative to time, and articulation of the foot in walking or running, angle of foot placement, leaning to one side, timing of foot placement while walking at a constant speed, pressure distribution across both feet, and other variations are discernible from the recorded gait characteristics. Also in one embodiment the system further comprises registration for medical and therapy practitioners, and registration by the registered medical and therapy practitioners of specific test subjects, for which profiles are created and maintained, including history of tests. In one embodiment the system further comprises a facility for scheduling tests by registered practitioners, and communicating information regarding scheduled tests to test subjects for whom the tests are scheduled. And in one embodiment the first plurality of pressure sensors integrated with the first article of footwear, the second plurality of pressure sensors integrated with the second article of footwear, the positioning circuitry communicating between the first article of footwear and the second article of footwear, the circuitry collecting readings from the first and second plurality of sensors, and from the positioning circuitry, as variables with respect to time, and communicating the readings to a computerized diagnostic apparatus, and software instantiating functions of the system, are packaged as a system to be sold or leased.

In another aspect of the invention a method for diagnosis is provided, comprising sensing pressure by a first plurality of pressure sensors integrated with a first article of footwear, the first article of footwear worn by a test subject on a left foot, sensing pressure by a second plurality of pressure sensors integrated with a second article of footwear, the second article of footwear worn by a test subject on a right foot, determining separation and direction of the first article of footwear relative to the second article of footwear, by positioning circuitry communicating between the first article of footwear and the second article of footwear, collecting readings by collection circuitry from the first and second plurality of sensors, and from the positioning circuitry, as variables with respect to time, communicating the readings collected to a computerized diagnostic apparatus, and processing the readings by the computerized diagnostic apparatus for a test period of time, determining gait characteristics for the test subject, including at least stride length and timing, and width of stance, and records the gait characteristics, time and date stamped, in a manner to be retrieved and displayed.

In one embodiment the method further comprises recording the gait characteristics associated with a test identification tag, and storing the gait characteristics associated with the test subject, creating a chronological record of multiple tests for the same subject. Also in one embodiment the method further comprises comparing gait characteristics for a test for the test subject with gait characteristics for the same subject in a previous test, and considering differences in diagnostic determination. Also in one embodiment the method further comprises a network-connected domain maintaining and updating gait characteristics for a plurality of test subjects, each test subject having a data profile wherein test results are stored chronologically, the network-connected domain executing software, providing access to the data to registered practitioners for diagnostic purposes.

In one embodiment of the method the method comprises arranging the first plurality of pressure sensors in an areal fashion relative to the sole of the first article of footwear, and arranging the second plurality of sensors in an areal fashion relative to the sole of the second article of footwear, providing pressure distribution readings from the sensors relative to time, such that timing for pressure application at distinct portions of the sole of the test subject's foot are recorded relative to time, and articulation of the foot in walking or running, angle of foot placement, leaning to one side, timing of foot placement while walking at a constant speed, pressure distribution across both feet, and other variations are discernible from the recorded gait characteristics. Also in one embodiment the method further comprises registration for medical and therapy practitioners, and registration by the registered medical and therapy practitioners of specific test subjects, for which profiles are created and maintained, including history of tests. in one embodiment the method further comprises scheduling tests by registered practitioners, and communicating information regarding scheduled tests to test subjects for whom the tests are scheduled. And in one embodiment the first plurality of pressure sensors integrated with the first article of footwear, the second plurality of pressure sensors integrated with the second article of footwear, the positioning circuitry communicating between the first article of footwear and the second article of footwear, the circuitry collecting readings from the first and second plurality of sensors, and from the positioning circuitry, as variables with respect to time, and communicating the readings to a computerized diagnostic apparatus, and software instantiating functions of the system, are packaged as a system to be sold or leased.

BRIEF DESCRIPTION OF THE SEVERAL VIEWS OF THE DRAWINGS

FIG. 9 is a diagram illustrating organization of a client profile in one embodiment of the invention.

DETAILED DESCRIPTION OF THE INVENTION

The inventors provide in the teaching of this application a unique human gait diagnostic and alert system that aids in patient diagnosis and performance analysis of regimens and specific medications or other treatments. The present invention is described in enabling detail using the following examples, which may describe more than one relevant embodiment falling within the scope of the present invention.

Figure 1:
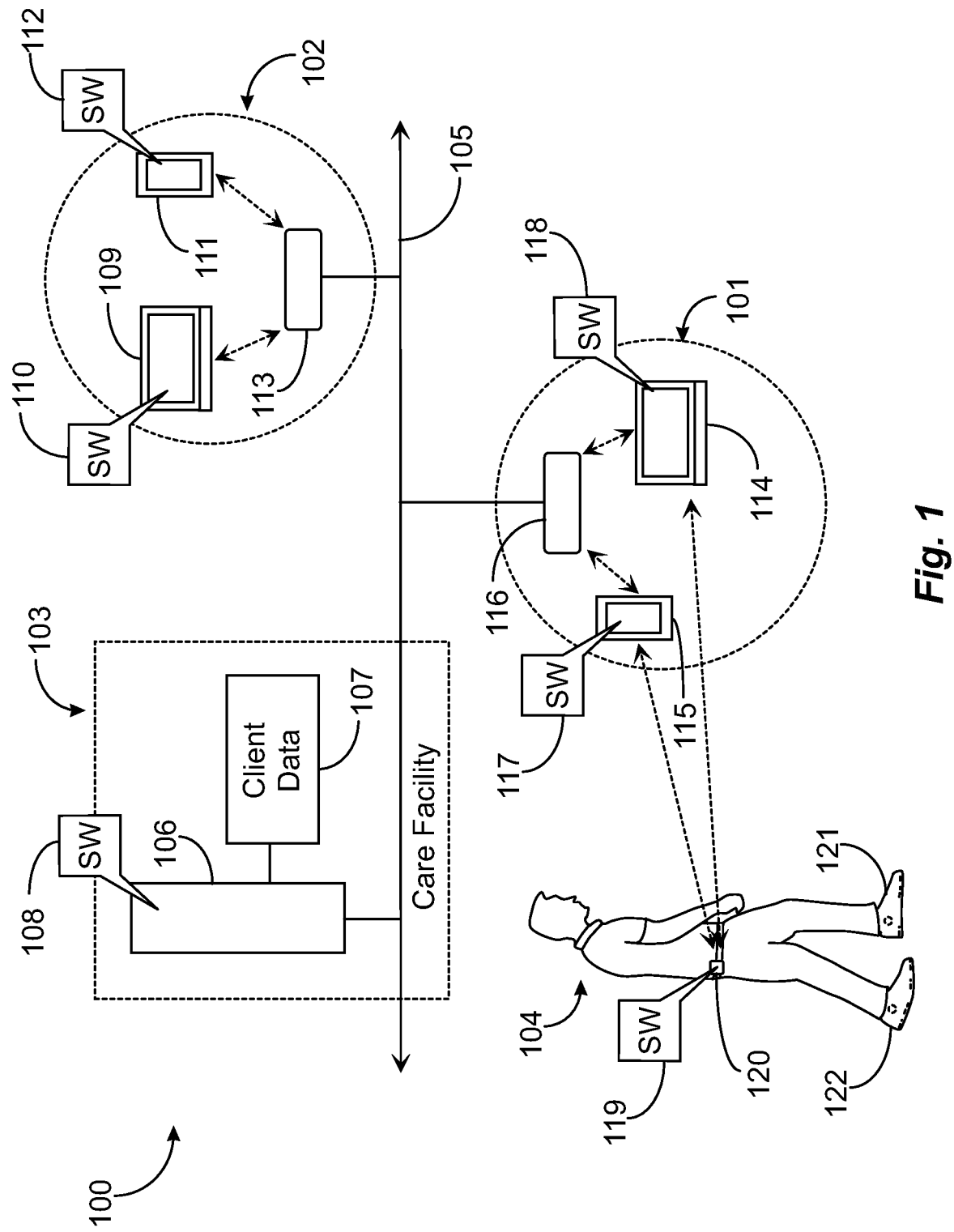
FIG. 1 is an architectural overview of a communications network over which human gait analysis me be performed according to an embodiment of the present invention.

FIG. 1 is an architectural overview of a communications network 100 over which human gait analysis may be performed according to an embodiment of the present invention. Communication network 100 includes a wide area network (WAN) 105, which may be the well-known Internet network. WAN 105, depicted herein as a network backbone, may be a corporate WAN, or a municipal area network (MAN) without departing from the spirit and scope of the invention. The inventor chooses the Internet as a practical example due to the public access characteristic of the Internet as a whole. WAN 105 represents all the lines, equipment, and access points that make up the Internet network, including any connected sub networks. Therefore, there are no geographic limitations to practicing the present invention.

WAN 105 supports a facility 103 that may be designated as a care facility, a physician office, a hospital wing for servicing outpatients or any other type of facility that may support remote testing and monitoring of human gait for clients that are registered or otherwise designated as patients or clients of the service in embodiments of the present invention.

Facility 103 is described here as an example of a network-connected domain where data may be aggregated and processed, and comparisons and determinations made, but is not limiting in the breadth of the invention. In other environments and circumstances, processing and determination may be more local to the subject being monitored, such as an athlete engaged in a game of football, basketball, rugby, and many other activities. Variations covering application of the invention in such circumstances is provided later in this specification.

A client of a facility like facility 103 is depicted herein as a client 104. Client 104 has, in this embodiment, a pair of shoes adapted with a variety of pressure, positional and motion sensors for measuring gait characteristics of the client. Client 104 has a left shoe 121 and a right shoe 122. Broken lines and circular boundaries in shoe 121 and in shoe 122 represent embedded sensors, the nature and location of which are described further below.

Client 104 has, in this example, a computing and data storage device 120 attached to a belt. Computing device 120 may include a processor, a power source such as rechargeable battery, and a port enabling offloading of data to another device or computing node having connection and access capability to the Internet. The data port may also support two-way communication. Device 120 may, in one implementation, be booted up by client 104 to activate sensors in left shoe 121 and right shoe 122. Device 120 may also comprise a processor, such as a microcontroller, a battery power source, a storage medium such as flash memory, wireless communications circuitry, and a memory to support at least one software (SW) application. A SW application 119 is provided in one embodiment and executed on the processor of device 120. SW 119 may be charged with communicating boot-up commands to the sensors in shoe 121 and 122, and sampling and data gathering procedures and schedules. Sensors collecting gait data may send the real-time data to device 120 through a wireless communications connection between the sensors and the device. In one implementation there may be wires connecting the sensors to the worn device without parting from the spirit and scope of the present invention.

Facility 103 in one embodiment comprises an Internet-connected server 106. Server 106 further comprises a SW application 108. Server 106 may be any server operated by a service provider having an interest in human gait analysis and diagnostic results that may come from such an analysis. In this implementation facility 103 is a care facility having access to medical files of client 104 specifically stored in a database 107 connected to the server. Facility 103 may be a doctor's office, an outpatient facility, a sports injury rehabilitation facility, or the like.

Client 104, in one embodiment, has a smart phone 115 and a personal Laptop computing device 114. Smart phone 115 has an Internet connection through a wireless network 101 and an Internet service provider. Laptop computing device 114 also has an Internet connection through network 101. Access to Internet 105 and server 106 may be provided through a universal gateway 116 connected to network backbone 105. Data in this example may be sent to server 106 by either device.

Smart phone 115 includes in this example a client software application 117. SW 117 may be a client application downloaded to phone 115 by client 104 as a registered client of the service provided through facility 103. Laptop computing device 114 may include a version of the client application 117 as client application 118. Client applications 117 and 118 provide an interface for client 104 to interact with facility 103 relative to testing gait, receiving medical advice and care, accessing patient records and information, and scheduling visits, tests, or other interactions that might ensue between client 104 and care facility 103.

Another wireless carrier network 102 is depicted connected to Internet 105 through a gateway 113. Network 102 includes a client smart phone 111 running a client application 112 and a client laptop 109 running a client application 110. These devices and hosted client applications represent third party clients that may be registered along with human 104 to the service of the invention and may be relatives or other concerned individuals, such as caregivers, who might be registered with facility 103 to receive alerts or other information relative to the condition or rehabilitative progress of client 104.

In this implementation, client 104 wears device 120 and special sensor-embedded footwear 121 and 122 while undergoing a period of gait evaluation. A benefit of remote monitoring of client 104 is that data may be taken during activity periods normal for client 104 at home or in a work or recreational environment away from home. Testing is not limited to being performed at a facility at a certain time and does not have to be witnessed by a third-party nurse or physician. In one implementation, device 120 may be booted or otherwise powered on by client 104 to activate sensors in the footwear to begin or resume collecting data. Human 104 may perform this activity as may be directed by a caretaker such as a monitoring physician or physical therapist. In one implementation, sensors may be wired to device 120 for power and communication. In one implementation, each sensor includes its own power source and wireless communications circuitry and can communicate collected data wirelessly to device 120 using such as a Bluetooth™ technology, or a near field communication (NFC) wireless protocol.

SW 119 may process sensor data as it is aggregated by device 120 to normalize the data for transmission over a wireless network. Wireless carrier network 101 is depicted in this example as a sub network to network 105. Device 120, aided by SW 119 may transfer data to another device, like a smart phone 115 executing SW 117 or to laptop 114 executing SW 118. In one implementation, device 120 is included as one node on a wireless network including smart phone 115 and laptop 114 as nodes. In this case data from device 120 may be transferred wirelessly to either phone 115 or laptop 114 or both. Client 104 may also access device 120 from either phone 115 or laptop 114 to update SW 119, to retrieve sensor data, or to alter commands to device 120 and SW 119 regarding sensor involvement and activation, length of active sensing period, or simply to update communications protocols.

Client 104 may use either smart phone 115 or laptop 114 to connect online with sever 106 to upload sensor data for analysis at the server with the aid of SW 108. Client 104 ay also use smart phone 115 or laptop 114 connect to and to download information from server 106. Client applications 117 (smart phone 115) and 118 (laptop 114) may provide a browser-based interface through which interaction with the service may be simplified and customized to client 104. In one implementation, SW applications 117 and 118 can process sensor data received from device 120 notifying client 104 about a finding in sensor data that might call for some action, follow-up, or alteration in sensing protocol or schedule.

In this implementation, server 106 hosting SW 108 performs analysis of received normalized data from phone 115 or from laptop 114. Results from analysis of data may be shared back over the network with human 104 smartphone 115 or laptop 114 and perhaps also with one or more third parties having authorization to receive and review gait data as represented herein by smart phone 111 running client application 112 and laptop 109 running client application 110. Server 106 aided by SW 108 may upload a statistical diagnostic model of a client that includes medical diagnostic information and one or more individual test models based on past gait monitoring or test sessions in a historical sense. Any medications and dose regimens of a client like client 104 may be accessible to server 106.

A gait test may be performed on a scheduled routine, and may be used to determine progression of a disease, effectiveness or non-effectiveness of a medication, progression of recovery from an injury, a propensity to falls, concussion, or other like goals that may be derived. A gait test may be customized for obtaining certain results where all sensors may not be used, but specific ones are involved. Gait tests or sessions typically include a time window and at least some instruction to the user, in this case client 104.

In one implementation a test is a routine, such as a list of commands, that may be downloaded as a SW-executable program and sent to device 120 for execution. Client 104 may review a test and gait requirements before sending the executable file to device 120 for implementation. Instructions may be given to the user relative to stride, heel to toe articulation, angle of foot, etc. as characteristics for focus while walking. In one implementation a gait test may include speeding up and slowing down, moving up or down an incline, making a series of right and or left turns, and so on. In one implementation, a test may call for natural uninstructed movement such as gardening, working in the yard, or other venues where natural movements are used during the task at hand. Any conceivable gait style might be considered, for example a skate board could be used, first propelling the board with the left foot and then switching over to the right foot. In one implementation, a walker, crutches, or a cane might be used where the gait analysis may determine which side to use a cane and what may be a best cane from a few test examples.

Figure 2:
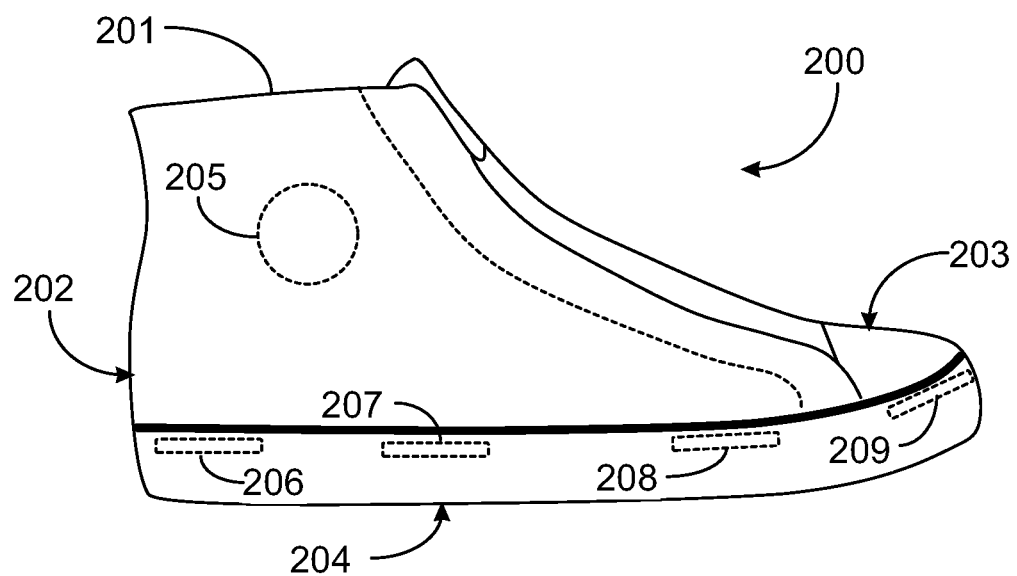
FIG. 2 is a side elevation view of a tennis shoe equipped with gait data sensors.

FIG. 2 is a side elevation view of a shoe equipped with gait data sensors. In one embodiment the sensors may be embedded in a sole 204 of the shoe, and/or fabric of a shoe or another type of shoe that may be worn by a test subject. Many different sorts of sensors may be used in different circumstances. In gait analysis there are important aspects to consider, such as stride length, stance (lateral distance between feet), articulation of the foot (heel to toe movement when planting a foot or walking), angle of foot placement (toe in or toe out), leaning of body to one side, timing of foot placement while walking at a constant speed, pressure distribution across both feet, and other considerations. As many of these considerations may have something to do with the physical health of the tested individual, the sensors used will collect these measurements and software will interpret these measurements against a model, which may be a standard model, or a custom model incorporating the client's current diagnostic predisposition at least and any onset condition from which the client may suffer.

Shoe 200 in FIG. 2 is, in this example, a right shoe that is a hi-top shoe with a top edge 201 that extends above the client's ankle. Other aspects of shoe 200, such as having lacings or not, or breathable fabric or not, cushy soles or not, may or may not play a part in diagnosing gait. In one implementation the invention may be practiced with sensor-embedded fabric foot coverings like a stocking, for example. Sensors are available in the art that measure pressure, position relative to another sensor, speed of motion, direction of motion, rotation of position, shock, shift, imbalance, and so on. Accelerometers, piezoelectric sensors, shim-based capacitive sensors, etc. may be used in any combination, including sensors that are printed on fabric that might be worn by the client.

In one implementation, there are sensors strategically placed and embedded at or near the top of the sole of the shoe in near vicinity to the sole and toe imprint of the client's foot. A heel region of the shoe 202 may include at least one sensor 206 that may measure pressure on and across the heel, shock on heel articulation during walking, orientation of the heel and speed of acceleration or deceleration of the heel in motion. A toe portion of shoe 203 may include at least one sensor 209 placed just beneath the toe grip area of the client's foot. At least one sensor 207 may be strategically placed ahead of the heel sensor and on the opposite side of the foot from the client's arch to measure pressure at the mid and outside portion of the foot. At least one sensor 208 may be strategically located ahead of the mid foot sensor, such as in the vicinity of the ball of the client's foot. At least one sensor 205 may be embedded in the shoe fabric and strategically located over the ankle and may measure rotation, lean, shock, motion, etc. of the client's ankle.

In one implementation, these sensors in one shoe may be controlled by a small microcontroller (not illustrated) that may also be embedded in the sole or in the fabric of the shoe and may have connection to the sensors for power and electric data acquisition. To communicate wirelessly for example, each sensor requires a wireless chip and a power source or a micro controller of the sensors in one shoe may be tasked with off-communication of the data collected. In one implementation, a small software (SW) or firmware (FW) component may be provided on a microcontroller charged with operating and collecting data from sensors, wherein the SW or FW may normalize sensor data and reduce redundancy in the data before offloading the data over a wireless link to a first processing unit such as component 120 executing SW 119 described above in the discussion of FIG. 1.

Figure 3:
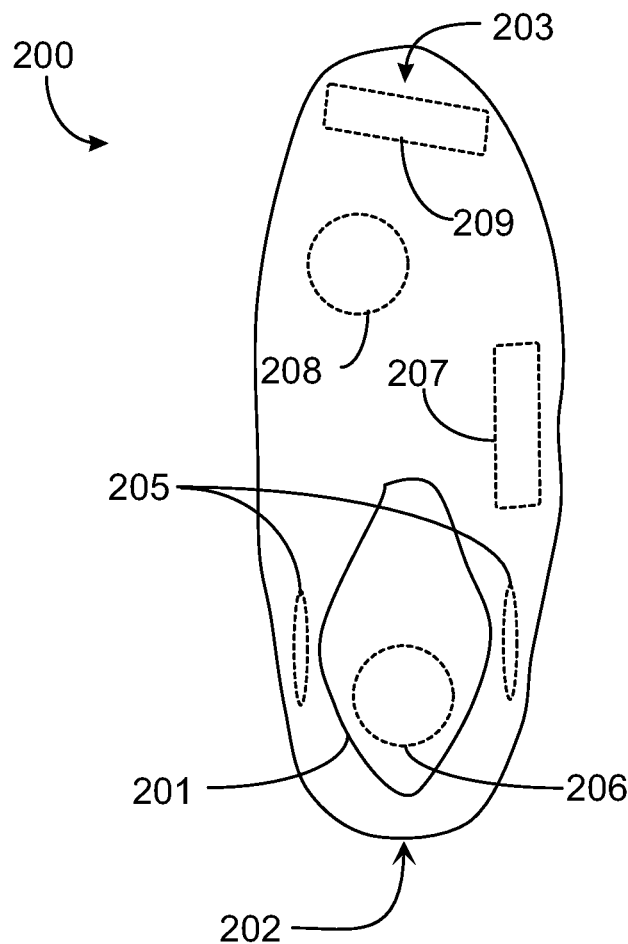
FIG. 3 is an overhead view of the tennis shoe of FIG. 2 depicting placement of sensors relative to the footprint of the shoe.

FIG. 3 is an overhead view of shoe 200 of FIG. 2 illustrating placement of sensors relative to the footprint of the shoe. In this view shoe 200 is viewed from an overhead perspective depicting area placement of the sensors within or just under the sole of the shoe, and placement of the sensors in the fabric at either side of the ankle region of the shoe. Sensor 209 is placed under the toe grip area of the foot. Sensor 208 is placed under the ball of the foot. Sensor 207 is placed about midway up the side of the foot. Sensor 206 is placed under the heel portion of the foot and sensors 205 (2 ea.) are placed at either side of the ankle in the shoe fabric. The top of the shoe 201 is just above the ankles in this hi-top shoe. In one implementation, a shoe having sensors and a stocking having sensors embedded therein might be provided whereas the stocking may include sensors such as sensors 205 that may not be included in the shoe. In one implementation, the stocking sensors may be connected to a micro controller in the shoe and may be attached to the outside of the stockings over each side of the ankle area to capture flex and rotation of the ankle while walking.

In one implementation, the sensors may occupy a special layer of material such as rubber, or some other flexible material that might be inserted into a shoe, thereby enabling the shoe as a host for a sensor sole pad. In another implementation, the sensors are permanently embedded into the shoe in a fabric layer provided within the sole of the shoe and in the shoe fabric about the ankles in a hi-top version. It is noted here that there may be additional sensors provided within shoe 200 without departing from the spirit and scope of the present invention. For example, a sensor might be placed in a stocking under the arch of a person's foot to measure flex strain on the client's arches in detection of and measurement of arch support provided by any shoe, such as a special orthopedic shoe designed for or selected for the client.

In one implementation, sensors from both the left and right shoe may communicate with one another relative to such values as position (orientation), or distance (stance). Information from both shoes may be offloaded to a processing device, such as device 120 running SW 119 of FIG. 1. While a client is engaged in walking during a test window, sensor data may be rapidly collected periodically or via streaming technology, so that distance variations and motion trends may be captured by the system as the client is moving.

Each sensor may, in one implementation, be calibrated for sensitivity and thresholds may be established for each sensor for reporting data. For example, in one application, like or counterpart sensors in each shoe, such as left and right sensors 207, may be calibrated to send distance data only when a particular distance threshold between them is exceeded during walking but will continually report pressure data with each step where that data is not controlled by a threshold. A difference in pressure data from left to right foot may reveal an anomaly in gait, where the client may be leaning on one foot more than another. Each sensor may be enabled to report orientation, such that if a client's foot placement while walking changes, such as foot turned out or in, those data points may be captured and analyzed. Motion may be captured, such as foot placement and articulation of the foot from heel to toe during walking.

Figure 4:
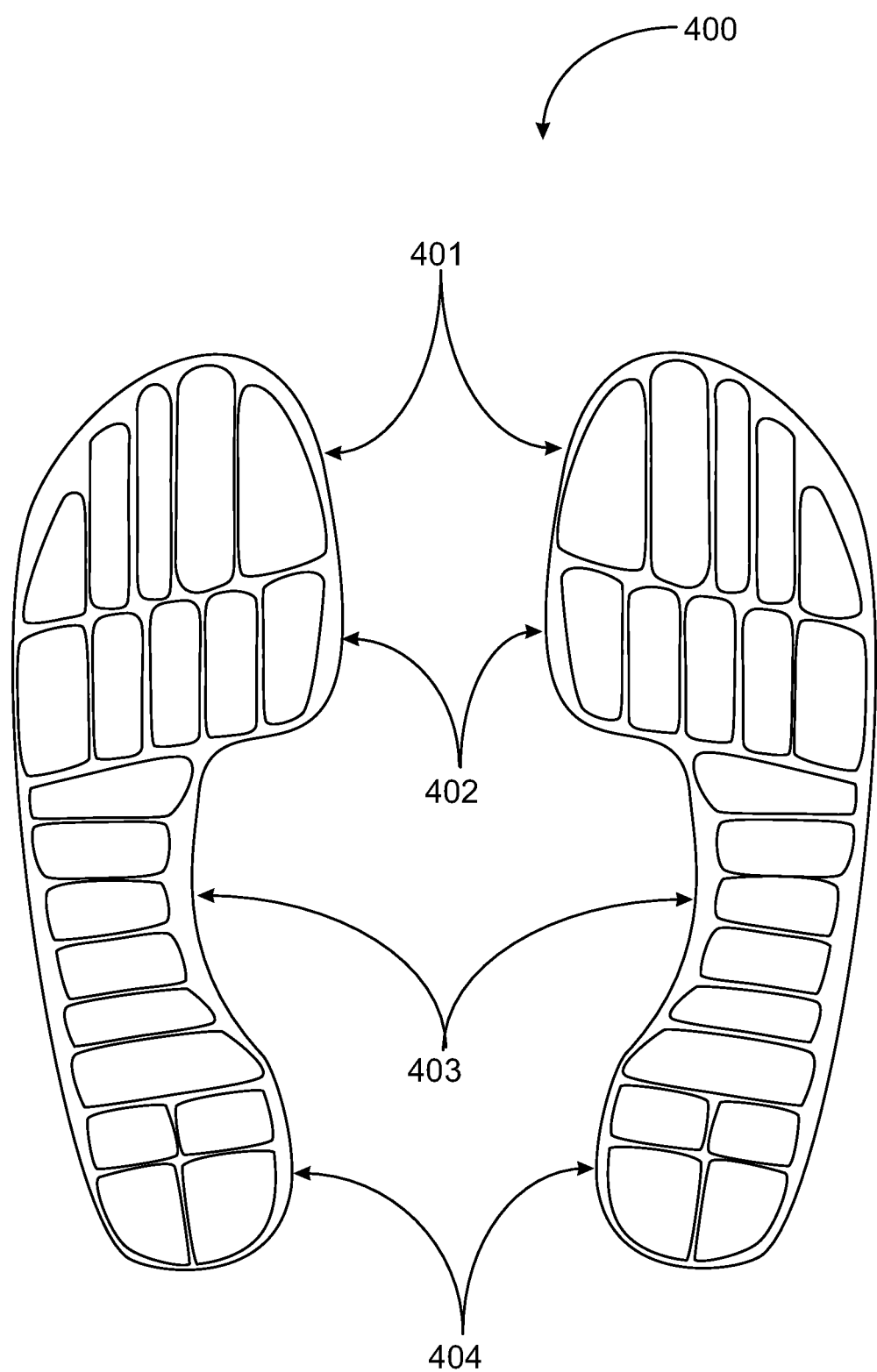
FIG. 4 is a bottom view of a pair of socks fashioned from sensor embedded fabric.

FIG. 4 is a bottom view of a pair of stockings 400 fashioned from sensor-embedded fabric. In one embodiment of the invention, a pair of sensor-embedded stockings 400 may be provided to collect sensor data for gait analysis. The inventor is aware of sensor fabric wherein sensors, micro controller and wireless communications circuits may be printed in a layer of perhaps one millimeter in thickness. In one implementation, stockings 400 may be worn by a client in place of or in addition to sensor-enabled shoes. Stockings 400 in this example include an array 401 of sensors in the toe grip area and the front ball portion of the user's foot. Stockings 400 also include an array 402 of sensors for the rear ball portion of the foot, extending completely across the foot to the outside of the foot. Stockings 400 include an array of sensors 403 for the arch portion of the client's foot between the heel and ball of the foot. Stockings 400 also include an array of sensors 404 covering the entire heel portion of the client's foot.

In this view, sensors along the side or even the top of the foot are not visible here, but may be assumed to be present in a pair of sensor-embedded stockings such as stockings 400. For example, there may be sensors over the ankle area of the client's foot embedded in fabric of the ankle area of the stocking in a same fashion as sensors 205 are embedded within the shoe fabric of shoe 200 in FIG. 2. In this example, the number and granularity of sensors might be greatly increased for producing accurate three-dimensional models of motion of each foot during testing. In another embodiment, the number and granularity of the sensors might be reduced in some cases where it may be acceptable from a diagnostic standpoint.

One with skill in the art of electronic devices will appreciate that there may be a separate microcontroller (not illustrated) provided in each sock of pair 400. Each microcontroller may also offload data to a remote computing device such as device 120 running SW 119 of FIG. 1. In one embodiment a client may, through a computing device having an input mechanism, calibrate sensors. In one implementation an application might be provided to a client's phone so that the client may check sensors, start and stop tests, calibrate the sensors, apply threshold values to certain aspects of a gait measurement, etc. For example, a threshold might be established wherein, if a gait stride becomes shorter than a preset distance, the system may begin measuring pressure data and heel to toe articulation and stance distance. In one embodiment, sensors are selectively operated, such as to measure stride distance and stance but not pressure. Selective operation of sensors may be common in execution of SW 119, to accomplish different desired purposes.

Figure 5:
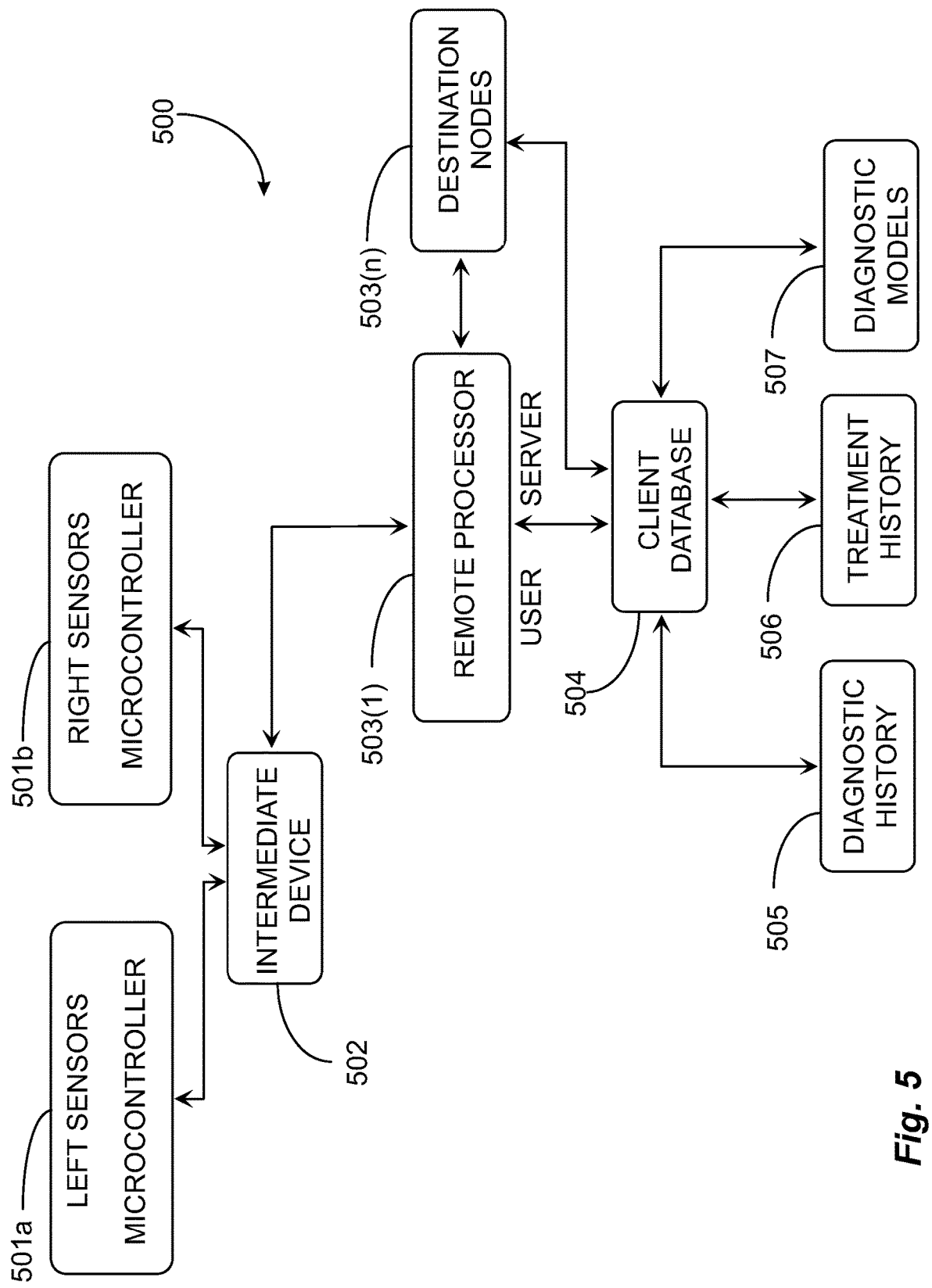
FIG. 5 is a block diagram depicting main elements of the gait analysis system of FIG. 1.

FIG. 5 is a block diagram 500, depicting elements of the gait analysis system of FIG. 1. Diagram 500 illustrates a system model that includes a left sensor and micro controller block 501*a* representing a left sensor-embedded shoe or stocking, and a right sensor and micro controller block 501*b*, representing a right sensor-embedded shoe or stocking. In this model each side, 501*a* and 501*b*, are separately controlled, with each having a microcontroller for powering and commanding the sensors, and for collecting and offloading the sensor data collected.

Data is aggregated to an intermediate device 502, analogous to device 120 of FIG. 1. The intermediate device may, in one implementation, be a Bluetooth™-enabled communications device having memory for temporarily storing the sensor data. Intermediate device 502 may also use wireless communications to transfer data to another device for processing, represented herein by a remote processor block 503(1). In one implementation, the intermediate device may be removed from a client and plugged into a USB port on a computing device, such as a laptop or desktop computing device, having a processor and SW for processing and analyzing the sensor data. In another implementation, intermediate device 502 may stream data to remote processor 503(1) as the data is collected.

In one implementation remote processor 503(1) is a device used or operated by the client, such as a smart phone or laptop computing device, with SW executing on the device using local data and resources to process and analyze sensor data during or after a test conducted. In one implementation, remote processor 503(1) may be a server connected to the Internet network executing SW for processing and analyzing the sensor data. Remote processor 503(1) may also be a third party-operated computing device, such as a doctor's laptop, a nurse's laptop, or that of a responsible caretaker or observer of the client.

Referring now to FIG. 1, server 106 may be analogous to remote processor 503(1). Remote processor 503(1) may perform most of data processing and analysis of the sensor data received from intermediary device 502. Referring to FIG. 5 in this example, remote processor 503(1) may have access to a client database 504 analogous to data repository 107 of FIG. 1. Remote processor 503(1) may be connected by a network, such as the Internet, to other computing nodes and or communications appliances functioning as nodes on the network that may serve as possible destination nodes **503(*n*), for information conveyed from remote processor 503(1). For example, if remote processor 503(1) is a server on the Internet, destination nodes 503(*n*) may represent any number of devices listening to or otherwise subscribing to node 503(1)** for information about gait analysis results processed for a client.

Destination nodes may be a primary doctor's computing device or that of one or more physician's assistants. Destination nodes may include family members of a client being tested or monitored for gait analysis. Client database 504 may include categorized information about a particular client of gait analysis. For example, client database 504 may include a diagnostic history data set 505 compiled over time for any gait analysis client. The diagnostic data may include known pre-existing conditions and general health characteristics of the client as compiled over time of treating the client. The client database may also include a treatment history data set 506 for the gait analysis client. The treatment history data may include all the treatment regimens, such as drug treatments, prescribed exercises, and so on, that the client has undergone over the same time period. Client database 504 may include a diagnostic model or models 507 for one or more or a combination of conditions, where the treatment data and the diagnostic history might be sub attributes of such a model. Model data set 507 may include, for example, an updated test model of expected gait analysis results that might be desired in treatment of the client, which the client is striving to achieve, such as a corrected posture during normal walking, for example.

In operation, collected sensor data from the left and right blocks 501*a* and 501*b* may be offloaded to intermediary device 502 for transfer to remote processor 503(1), where the data may be analyzed and processed using diagnostic models 507 to determine differences and areas for improvement. A gait analysis test may take any custom form, as it may be created for and customized for a client considering known conditions and symptoms of the client. For example, a gait analysis test might be created for a client who suffers from severe arthritis in the hips, and the purpose for gait testing is to see how well a certain medication is working to improve mobility of the patient in walking. A model of the subject's gait might be created from data recorded before taking a medication. A predictive model might then be created that depicts a goal of improvement for the medication. Once on the medication, a series of subsequent tests might be performed by the client and reported for processing and analysis against the predictive model to determine if the patient has improved in mobility, balance, posture, and so on. In a variation, tests may be performed on different medications to determine which medication improves mobility for the client at a more satisfactory level.

Once the data is analyzed and processed, results may be made available to certain parties, such as doctors, family members, nurses, and so on, who may be included in that client's network. In one implementation, remote processor 503(1) may be a device operated by the client locally in certain embodiments where the client is not at risk, such as a runner using the system to improve endurance or speed, or to improve posture to reduce injury or wear. So, in one aspect, the gait analysis system may be used in various sports industries as a training tool to improve performance and to reduce injury. If a client has a sports injury or is in a rehabilitative environment, the gait analysis system might be used to help the client regain lost mobility, such as after a stroke or some other event that may compromise balance and mobility of the client.

Figure 6:
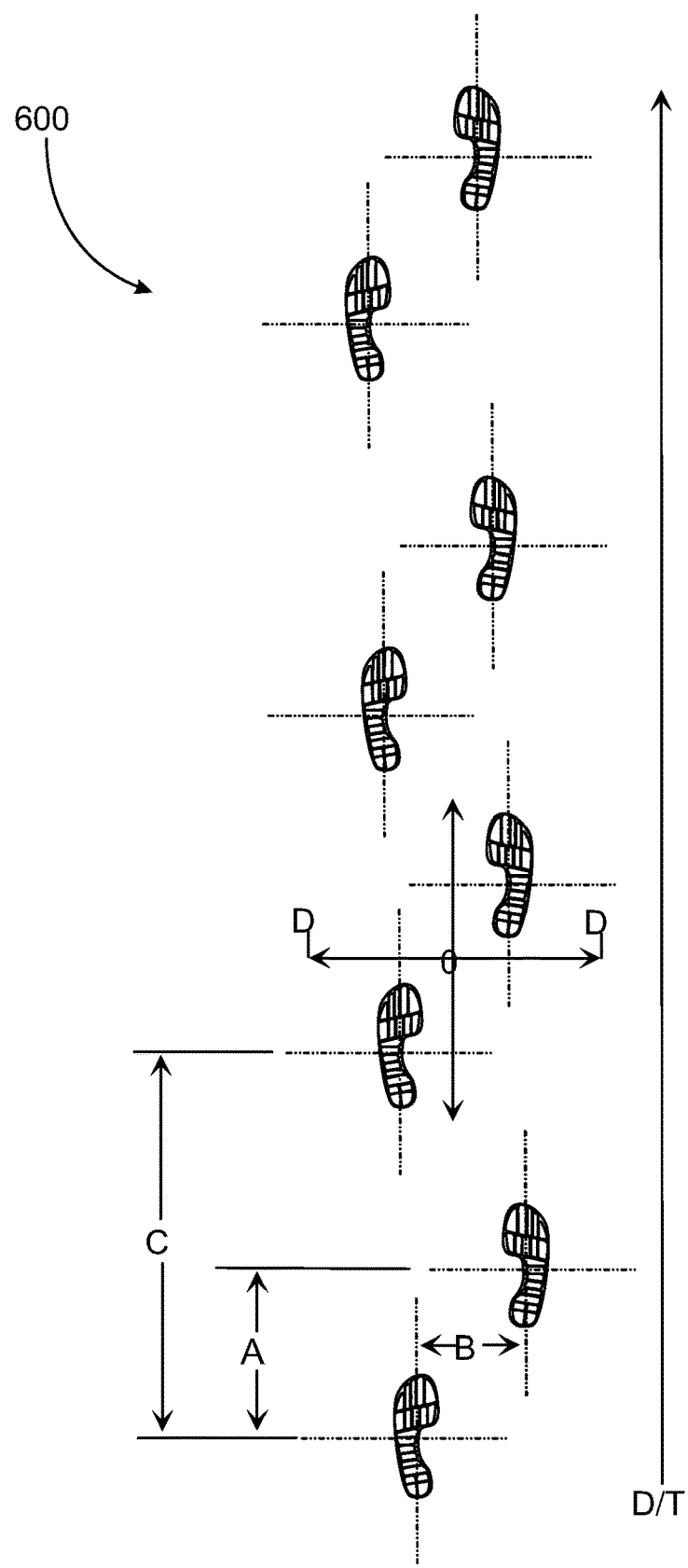
FIG. 6 is a block diagram depicting point of positional measurement by sensors over time and distance.

FIG. 6 is a diagram 600 depicting points of positional measurement by sensors over time and distance. Diagram 600 depicts a distance/time line (D/T) and a series of recorded steps by a client that may be under test. In this chart, important points of measure may include the distance between alternate steps made by the gait analysis client as distance A. The analysis may look for difference in A that may repeat alternatively of time and distance of the gait. The sensors may also record lateral distance B between the user's feet (stance) and may record instances of wider or narrower stance measurements during a trial.

The sensors may also record distance between plants of a same foot such as distance C during a normal gait, and may record differences, and may compare with like measurements from the opposite feet. In one implementation, a threshold value might be introduced into a gait analysis test, such as a measurement D, representing an outer threshold distance for stance. For example, a person who is elderly and becomes more afraid of falling, may shorten the stride and may tend to walk more flat-footed, placing the feet flat on the floor with less articulation from heel to toe. The width of stance may also be widened to provide a more stable platform. In a case of an introduced threshold, if sensors record a stance measurement that falls into or exceeds the threshold, an alert might be generated to the client, a doctor, or to a caretaker. Introducing a threshold may be useful for a nurse, for example, that may be monitoring the walking of one or more clients, where the monitoring is remote from a nurse's laptop or desktop system, and the nurse may see any alert or signal relative to the walking client. In such a case, a nurse might be alerted to a situation, such as the patient tiring. The monitoring nurse would get an alert and a location of the patient. A nurse could monitor more than one patient walking simultaneously, so being right beside the patient may not be required. A group rehabilitation class may utilize such scaling of the system.

Figure 7:
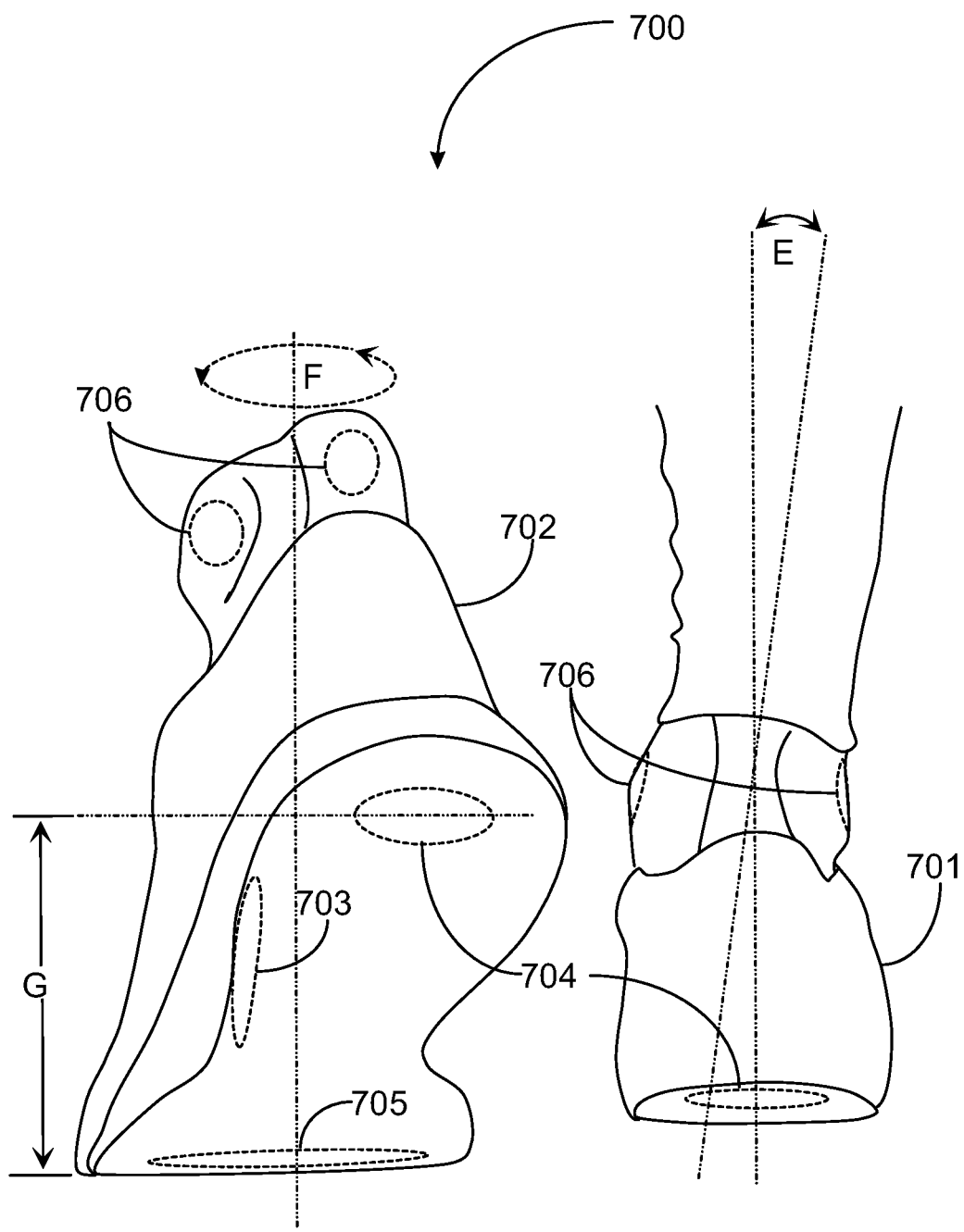
FIG. 7 is a rear view of a pair of tennis shoes depicting further points of positional measurement relative gait according to an embodiment of the invention.

FIG. 7 is a rear view of a pair of shoes 700, depicting further points of positional measurement according to an embodiment of the invention. Shoes 700 include a left shoe 702 and a right shoe 701. In this view, left shoe 702 is articulated, with the heel off the ground in preparation for a next step. Toe grip sensor array 705 and heel sensor array 704 have a positional relationship in foot articulation that may be captured relative to motion. Measurement G records that motion and may record a maximum height G that may be repeatable before the user lifts shoe 702 completely off the ground. Sensor arrays 706 about the ankle of the client may record rotation F of the ankle, and may be attached to or embedded within stocking fabric or shoe fabric.

Shoe 701 in this circumstance is planted firmly on the ground, where the position of sensor arrays 706 about the client's ankles records an angle of lean out E of the client's leg above the ankle out from center line. Many other positional measurements may be recorded during walking or running, such as toe-in or toe-out, leaning relative to the upper body toward the outside of the ankle or inside of the ankle, leaning forward with respect to walking pattern or leaning backward with respect to walking pattern. Algorithms in the SW that analyzes the gait may be employed to isolate data that are out of normal or otherwise might represent an anomaly if those recorded measurements are repeated more than an acceptable number of times during gait analysis over distance and time.

Gait analysis in embodiments of the invention may be performed in a way that considers historical data for a client, including diagnostic data, general data about diagnosis and progression of a condition, historic gait analysis data, and so on, to make decisions and predictions regarding the effectiveness of a medication or physical regimen, or the time period when one medication should be switched for another, or if medication should be stopped or started, for example. Gait analysis may be used to gather information about how a variety of human conditions that might affect the gait, whether the person may be progressing or regressing relative to a condition, including for example, stroke, brain tumor, sciatica, arthritis, partial paralysis, diabetes, heart conditions, Parkinson's disease, dementia in its various forms, concussion, or a combination of such conditions.

Gait analysis may aid in therapy, such as for healing of broken bones, prosthesis management, sports injury recovery, stroke recovery, and so on. In some cases, gait analysis may reveal new symptoms that are identified in repeated patterns, where there was no prior diagnosis available, and where identified patterns may aid in a quicker diagnosis of a condition just beginning to affect the client. In one embodiment, calibration of the sensor arrays may be performed with a client who has a healthy gait and is not the person who will undergo analysis. In such a case a comparative model of a healthy stride for a person who is the same weight and height as the test subject may be created and used as a goal pattern or model for the test client.

Figure 8:
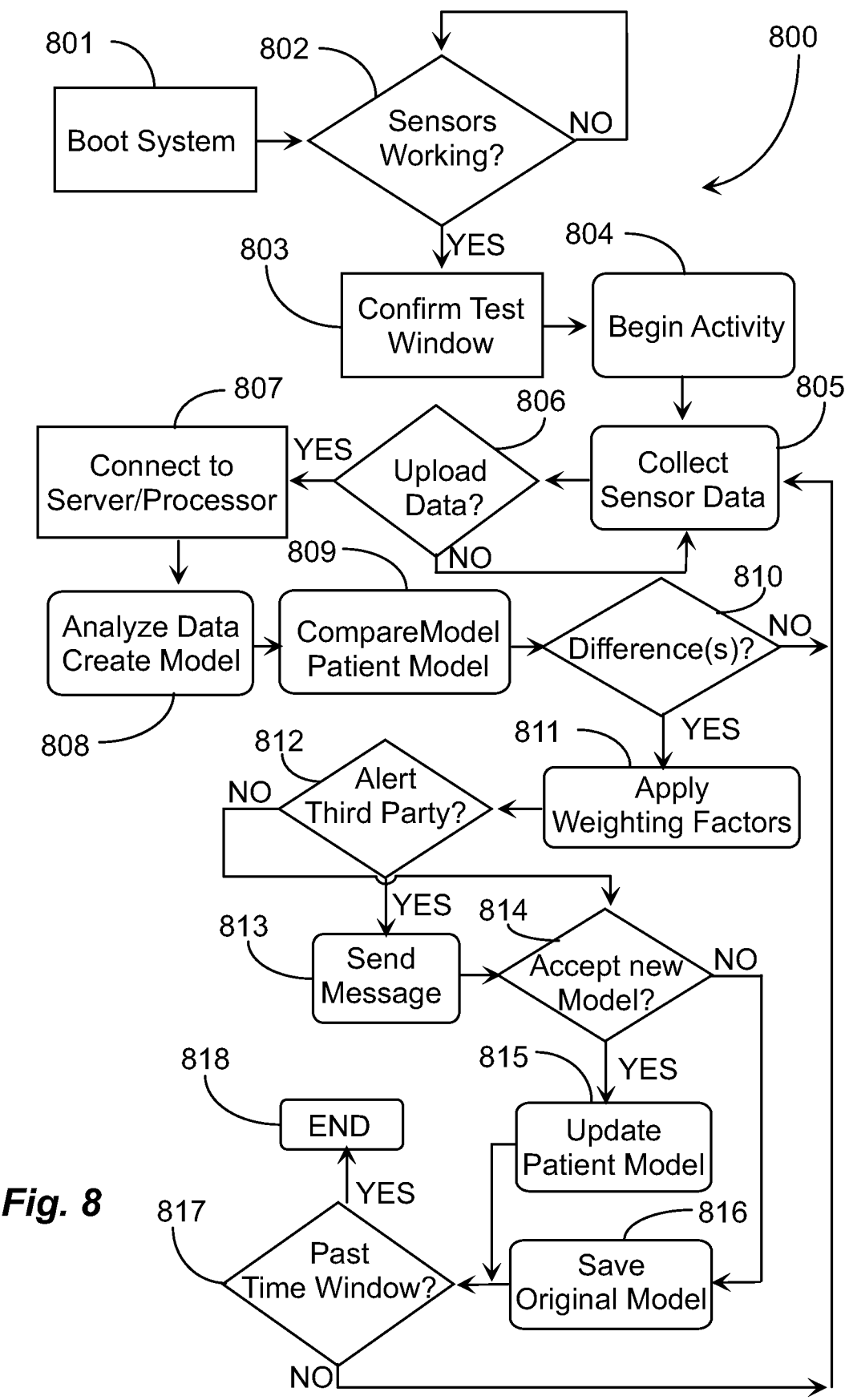
FIG. 8 is a process flow chart depicting steps for measuring gait of a human and updating system data and alerting defined parties according to an embodiment of the invention.

FIG. 8 is a process flow chart 800 depicting steps for measuring gait of a client, updating system data, and alerting designated persons according to an embodiment of the invention. It may be assumed for purposes of discussion that a gait analysis client may be responsible for booting the system in step 801. In one aspect, a doctor may provide the gait system to the subject as part of a treatment or diagnosis program, wherein the subject boots the system and follows other instructions such as setting a time window for the analysis. Analysis might be performed on a treadmill at the client's home, or it might be performed while the client walks around a block out of doors. In other aspects a clinical setting may be required, and a nurse, or other practitioner, may boot the system.

Booting the system in step 801 might be accomplished by powering on an intermediary flash-based storage device having connectivity to the sensor-embedded shoes or stockings, such as device 120 aided by SW 119. Booting the system may involve a wireless signal. The sensors may be powered locally, and may remain in a sleep mode when not in use. In one aspect a switch for each sensor-embedded shoe or stocking might be provided locally, such as attached to or otherwise accessible from the shoe or stocking. The intermediary device may also be powered on separately.

In step 802, the intermediary device may determine if all the sensors are working. A small light emitting diode (LED) display may be provided on the intermediary device, where a green light may indicate that all sensors are working. A yellow light may indicate that one or more sensors need calibration, are producing error values, or are not responding at all. In one implantation, a scroll function might be provided to a display on the intermediary device to scroll through displayed information, such as which sensor array may need attention. A function may also be provided for data input into the intermediary device, such as setting a time window for the analysis.

If at step 802 there are sensors that are not working or reporting errors, the process may loop back until all the sensors are working and responding correctly. If at step 802 all the required sensors are responding, then the process may move ahead to step 803, where the test window may be confirmed. In one aspect of the method, an intermediary device might be a client's smart phone enabled through SW and wireless communications capability, such as Bluetooth™, to communicate with the sensors and receive data from the sensors or from a microcontroller operating each set of sensors.

At step 804, the gait analysis client donning the sensor-embedded shoes or stockings may begin activity. As the client begins, the sensors record data and the intermediary device collects the sensor data at step 805. In one aspect, the sensor microcontrollers may normalize sensor data before transferring the data to the intermediary device. A microcontroller running a firmware or software algorithm may average data, delete some data, prioritize data, and so on. In another aspect, the data may be partially processed at the intermediary device, where it may be received in raw stream format. In one aspect of the method, the intermediary device may relay or forward the data to a remote processing device in real time. In another aspect, the intermediary device may simply cache the data temporarily for later upload to a computing device for remote processing of the data.

A determination may be made at step 806 whether to upload data to a remote processor or to a local device for remote processing, depending, in some circumstances, on whether set thresholds have been met or exceeded. It may be assumed that at this decision point, the collected data is at the intermediary device. If at step 806 the determination is not to upload data then the process may loop back to step 805 to continue collecting data. In one aspect the time window for the test may still be running and data is uploaded after the test has been concluded. In another aspect the sensor data may be streamed in real time during the test window to a remote processor locally for analysis and processing of results. If at step 806 it is determined to upload data, then at step 807 the intermediary device holding the collected data may be accessed wirelessly or by physical connection to a computing device serving as the remote processor. In one aspect, the intermediary device may communicate the data to a smart phone or to a laptop operated by the client or by a person cooperating with the client, who may then establish a network connection and send the data to a server on the network for remote processing.

At step 808, the data may be analyzed and a data model representing the collected data may be created. Such a model may represent dimensions and motion in three dimensions. Such a model may be visualized as a simulation or may be read as a data model. At step 809 the system, aided by SW, may compare the created model to an existing model created previously, or to another model such as a goal model created using the subject's dimensions, but synthesized to a healthy, stable and balanced gait toward which the client might be working. Using comparative analysis can quickly identify differences in the data characteristics between the models.

At step 810 a determination may be made relative to identification of any differences between the subject model and the existing model for comparison. An existing model may be the clients immediately preceding test recorded for which a model was created. An existing model may be a synthesized model, or one created using the client's likeness and test procedure, but adjusted to reflect an ideal or desired model of a gait to which the subject may aspire.

If it is determined that there are no significant differences between the models, the process may loop back to further data collection, perhaps running a second test or expanding the time of the current test to collect more data. If at step 810, differences of note are identified in comparison, the processing system may apply an algorithm with or without weighting factors at step 811 to characterize the differences according to expected or predicted results that are meaningful to the client, the client's doctor, and to other parties having authorization to the client's data.

A weighting factor may be the age of the client, a stage of diagnosis of the client, a current dosage of a drug the client may be on while tested, or other characteristics or attributes of the experience or state of the client. An algorithm may be used to determine if model differences may result in a request for diagnosis, a change from one stage to another (regression or progression), a selection of other tests to perform, a reduction or increase in a medication the client is taking, and so on. At step 812, a determination may be made whether to alert a third party or more than one third party, to results, which might include an analysis summary, advice, a warning, further instructions, and so forth. If at step 812 it is determined that there is no need to notify a third party, the process may resume without performing step 813. If at step 812, it is determined that one or more third parties need to be consulted or informed, the process moves to step 813, where communication such as messaging, emails, or voice calls might be generated and communicated to the one or more third parties.

At step 814 it may be determined if the system will accept the latest model for a new test as a new patient model or as a new comparative model to use as a standard to compare with a future test. In one aspect, older data models no longer relevant might be deleted. If the system determines not to save the latest data model then the process may skip to step

816, and the last or original data model might be saved. It may be that new data showing differences may not have been significant to change the existing model. If the system determines to accept the new data model the patients model may be updated or overwritten with the new data at step 815. It may be appreciated that all this processing may occur in real time as a patient is still being tested and data is still being collected.

At step 817, it may be determined that a test time window has expired for the current test. If it has not yet expired, then the process may resolve back to step 805 collecting data. If at step 817 it is determined that the time has expired, and the gait test is over, then the process may end for that client in step 818. Whether data from the sensors is processed in real time as it is received, immediately after all the data is received, or later after the data is received and stored, may be a matter of instruction and purpose of gait testing for a client.

In other aspects, gait analysis using the elements and functions of the present invention may be conducted in an athletic environment. For example, equipment including sensors as described above may be worn by football players, and broadcast to system computing devices on sidelines. There may be separate systems used concurrently for players to accommodate available bandwidth. It may be important, for example, to monitor a player who has suffered a head impact event to immediately detect differences in gait and stride after the event to determine if there might be symptoms of a concussion. Each player may have a comparative model on file for comparison.

Such a system may be utilized for training and education in real time, such as to teach better posture while walking, wherein the sensors may detect body lean forward to the side or to the rear compromising good posture. In another example of a sports application, a test model may be created in the likeness of a bowler, where the model is synthesized to an ideal bowler's approach, steps, stride, and so on, in steps to release the bowling ball. Comparing this to a real bowler's data can provide information to the real bowler as to how to improve performance. This information may be provided in the bowler's ear after the tested roll and before the next roll. Information may be audible such as tighten your grip, straighten your angle, take shorter steps with the swing of the arm, extend more, etc. The same may be said for wide receivers, quarterbacks, or any other sport where gait plays a role in success, or in detecting a problem before it becomes acute. For example, in basketball, a player over-extending an ankle might be monitored afterward to determine if that event will affect play enough to remove the player. There are many possibilities.

In many embodiments of the present invention, regardless of the nature of the subject for which gait analysis may be made, such as a resident of a nursing home, or a professional athlete, the system of the invention is personalized to an individual subject. For example, it was described above, referring to FIG. 1, that client data is stored in a data repository 107. Expanding on this concept, in many embodiments of the invention a personal profile is developed for a client, and applications of the invention are dependent on data and information in that personal profile. FIG. 9 is a diagram of an exemplary client profile 900, shown divided into different categories of information and data.

One data type is client identification, which may include data points such as name, email address, mailing address, telephone numbers, Facebook™ URL, and other such ID data. In one embodiment of the invention each individual client also is tagged with a Matter Number. Another data type is Categorization, which may be senior citizen, disabled person (nature of disability), athlete, fireman, policemen, etc. Yet another data type is Affiliation. The client may be, for example, the POTUS, a star NBA basketball player, a resident of a particular nursing facility, and so on. There may well be more than one affiliation.

As this data repository in many embodiments exists to facilitate use of gait analysis equipment, there will be a Test History of results of various tests using apparatus and software of the system. The history may include test types taken, date and time, number of repetitions, and so on. There may further be data points related to test scheduling. For example, tests to be performed by this client in a near future. In some embodiments there may be a current primary focus, describing the main goal or plan of the system for this client. For example, a focus may be: improve her base-stealing ability. There will be a DATA section for recording all tests, results, predictions, and so on, in a manner that same may be retrieved by a search function.

In one embodiment of the invention, whenever a new entry is made in a profile for Test Scheduling, which entry is required to identify the client, the type of test, and the date and time for the test to be performed, an update is made to a universal scheduler in the system, which is programmed to alert the client in various stages as to an approaching need for a test that has been scheduled. The profile has contact info, such a email addresses and phone numbers, and a client can indicate a preference for alerts. At a substantial time before a test is scheduled the Universal Scheduler will inform the client of the date and time for the test, and any special requirements for clothing, and so on. Alerts are then made at escalating periods before the test.

The scheduler is informed if a client shows up, or misses an appointed test, and may be programmed to inform the client accordingly. Tests met and performed are recorded as to results, back into the client's profile, and may also be communicated to other registered recipients, for example the client's primary physician.

In one embodiment of the invention mechanisms are provided for clients to register directly to the system at facility 103 (see FIG. 1). More specifically, however, registration at Domain 103 is by medical enterprises, physicians, physical therapy practitioners, and the like, who will register their own clients to the system. In this case the client profiles will be organized with profiles for all the clients for a particular physician or other practitioner or enterprise, and the profiles will be associated in the database with the particular physician, practitioner or enterprise.

In another embodiment of the invention, systems of the invention, including testing apparatus, communication apparatus and software, and database system and software for operation in all forms, may be provided to enterprise applicants in a manner that the enterprise buying or leasing the system may set up and operate a system according to embodiments described herein in enabling embodiments, and may be licensed to use the system. In this embodiment setup help may be provided in any one or combination of different forms.

Figure 10:
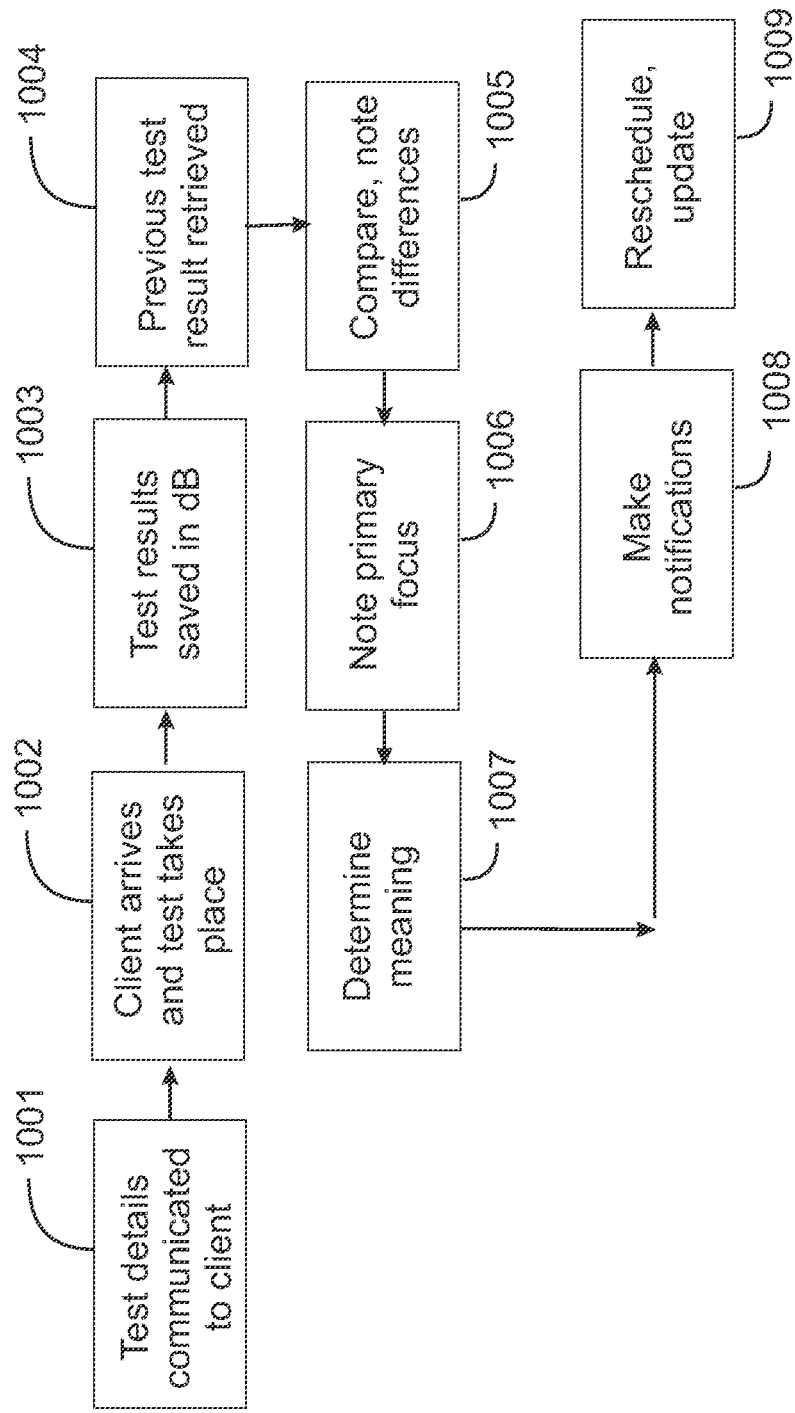
FIG. 10 is a flow chart of operation in one embodiment of the invention.

FIG. 10 is a flow chart depicting operation of the system in one example. The process assumes that a client has a profile, associated with a Practitioner X, and that a test has been scheduled for the client.

At step 1001, test details are communicated to the client. In this communication, the date, time and place for the gait test is included, as well as any special information, like clothing to be worn, for example. Alerts for the test may be repeated at escalating intervals.

At step 1002 the client arrives for the test, is prepared for the test, and the test is conducted. At step 1003 test results are saved in the dB, in the profile for the client. At step 1004 results from a previous test are retrieved. At step 1005, the previous results for a similar, or same, test are compared, and differences noted. The differences may indicate, for example that the client's gait characteristics have changed since the previous test. For example, the client may be taking shorter steps at a wider stance, which might mean that the client is developing an increased fear of falling.

At step 1006 the system notes the primary focus, such as "client is recovering from a concussion". This focus may branch the system into a particular series of events. In some cases, a human evaluation may be made from the comparison. In some embodiments there may be analysts associated with the system, who may manually note the results and comparisons, and may have a portal for entering information. There may also be automatic responses in the system to certain differences that may be noted.

At step 1007 meaning is determined. The test result and comparison with previous tests may be determined by an associated practitioner to mean that the client is fully recovered from a concussion, for example, and may not need further testing.

At step 1008 notifications may be made, such as by email, text, or voice mail. An associated practitioner, such as practitioner X, with whom the client is associated, may be m notified, as well as the client, caregivers, and other persons associated with the client, and for whom the system is configured to respond. Once notifications are made, rescheduling and updating of data, schedules and the like, for the client, may be done as a final step 1009. The system then monitors schedules for any next test for the same client.

The skilled person will realize that the process depicted in FIG. 10 is but one of many such processes that may be implemented in different embodiments of the invention. The steps may vary, and the order may vary as well.

In many embodiments of the invention analysis and reporting, as well as further testing and the like, is based on the comparison of results of configured tests administered to a specific client, rather than on norms or standards determined over a plurality of client results and tests. The present invention is made to be, and meant to be, personalized to a single client. This is partly because deviation from a standard by one client may or may not indicate a particular result, but deviation by a client from his or own previous performance may be trusted to have specific meaning.

In other embodiments of the invention the gait analysis system, or parts of it, may be used for real-time determination of such as concussion, fatigue and the like in, for example, athletic situations. As a specific example, a football player may have monitoring footwear operational, as described in other parts of this specification, along with a broadcast device, such as element 120 in FIG. 1, and the comparison and analysis functions may be provided by a computerized station on the sideline of the football field, or nearby in a locker room, for example. In this example, a normative characteristic for the client may be recorded, and may be an average over a number of plays in a game. This normative characteristic may be compared in real time with continuing analysis of the player's (client's) ongoing recording of gait characteristics. A serious deviation may well indicate an anomaly, like excessive fatigue, a hamstring injury, a concussion, or any number of other potential problems. Alerts may be immediately sent to trainers, coaches and the like. The same kind of processes may be applied to basketball, gymnastics, rugby, or any other sport.

In some embodiments of the invention the system, or parts of it, may be used as a training aid and guide, wherein, for example, a pass-reception pattern or maneuver may be recorded, and a player's performance of the pattern or maneuver may be recorded in practice and compared, with differences communicated back to the player, with suggestions for closer adherence to the pattern. Training may be done in nearly any sport in a like manner.

It will be apparent to one with skill in the art that the gait monitoring and alert system of the invention may be provided using some or all the described features and components without departing from the spirit and scope of the present invention. It will also be apparent to the skilled artisan that the embodiments described above are merely examples of a single broader invention that may have greater scope than any of the singular descriptions taught. There may be many alterations made in the descriptions without departing from the spirit and scope of the present invention.

It may be further apparent to the skilled person that the arrangement of elements and functionality for the invention is described in different embodiments in which each is exemplary of an implementation of the invention. These exemplary descriptions do not preclude other implementations and use cases not described in detail. The elements and functions may vary, as there are a variety of ways the hardware may be implemented and in which the software may be provided within the scope of the invention. The invention is limited only by the breadth of the claims below.

The invention claimed is:

1. A system for gait analysis, comprising:
    a first plurality of pressure sensors integrated with a first article of footwear worn by a test subject on a left foot, the first plurality of pressure sensors positioned in the first article of footwear sensing pressure at different positions in the footwear;
    a second plurality of pressure sensors integrated with a second article of footwear worn by a test subject on a right foot, the second plurality of pressure sensors positioned in the second article of footwear sensing pressure at different positions in the footwear;
    a first position sensor in the first article of footwear and a second position sensor in the second article of footwear, the first and second position sensors being configured to wirelessly communicate with one another to enable sensing separation of the first article of footwear relative to the second article of footwear, and report position measurements as a function of time and timing of foot placement while walking at a constant speed;
    a data-gathering and processing device in wireless communication with the first plurality of pressure sensors, second plurality of pressure sensors, first position sensor and second position sensor, the data gathering and processing device being configured to gather data from the first plurality of pressure sensors, second plurality of pressure sensors, first position sensor and second position sensor and pre-processes the data and associate said data with an identity of the test subject; and
    a network-connected server in communication with the data gathering and processing device, the network-connected server having a data repository storing information regarding individual test subjects, the network-connected server being configured to 1) receive the data associated with an identity of the test subject from the data-gathering and processing device, and 2) execute software including an algorithm that performs gait analysis from the stored information regarding individual test subjects and the received data associated with an identity of the test subject and 3) store results of the gait analysis in the data repository.

2. The system of claim 1 wherein the results of the gait analysis are recorded associated with a test identification tag, and stored associated with the test subject, creating a chronological record of multiple tests for the same subject.

3. The system of claim 2 wherein results of the gait analysis for a test for the test subject are compared with results of the gait analysis for the same subject in a previous test, and differences are considered in diagnostic determination.

4. The system of claim 3 further comprising a network-connected domain maintaining and updating the results of gait analysis for a plurality of test subjects, each test subject having a data profile wherein the results of gait analysis are stored chronologically, the network-connected domain executing software on a processor of a server in the domain, providing access to the data to registered practitioners for diagnostic purposes.

5. The system of claim 4 wherein the network connected domain presents an interactive interface enabling registration for medical and therapy practitioners, and also registration by the registered medical and therapy practitioners of specific test subjects, for which the medical and therapy practitioners create and maintain profiles for the specific test subjects, including history of tests.

6. The system of claim 5 further comprising a sub-system enabling registered practitioners to schedule tests for test subjects, and to communicate information regarding scheduled tests to the test subjects for whom the tests are scheduled.

7. The system of claim 1 wherein the first plurality of pressure sensors is arranged in an areal fashion relative to the sole of the first article of footwear, and the second plurality of sensors is arranged in an areal fashion relative to the sole of the second article of footwear, providing pressure distribution readings from the sensors relative to time.

8. A method for diagnosis, comprising:
sensing pressure by a first plurality of pressure sensors integrated with a first article of footwear worn by a test subject on a left foot, the first plurality of pressure sensors positioned in the first article of footwear sensing pressure at different positions in the footwear, the first plurality of pressure sensors in wireless communication with a data-gathering and processing device, reporting pressure readings as a function of time;
sensing pressure by a second plurality of pressure sensors integrated with a second article of footwear worn by a test subject on a right foot, the second plurality of pressure sensors positioned in the second article of footwear sensing pressure at different positions in the footwear, and in wireless communication with the data-gathering and processing device, the second plurality of pressure sensors reporting pressure readings as a function of time;
determining separation and direction of the first article of footwear relative to the second article of footwear by position sensors in the first article of footwear and in the second article of footwear, the position sensors sensing separation of the first article of footwear relative to the second article of footwear, the position sensors reporting position measurements as a function of time and timing of foot placement while walking at a constant speed;
collecting the readings by the data gathering and processing device as variables;
communicating the readings collected to a network-connected server in communication with the data gathering and processing device, the network-connected server having a data repository storing information regarding individual test subjects, and executing software including algorithms that perform gait analysis from data associated with individual test subjects; and
determining gait characteristics and anomalies for the test subject by the network-connected server, including at least stride length, foot placement timing, and width of stance, and recording the gait characteristics in the data repository, time and date stamped, in a manner to be retrieved and displayed.

9. The method of claim 8 further comprising associating the gait characteristics with a tag identifying a specific test, and storing the gait characteristics also associated with the test subject, creating a chronological record of multiple tests for the same subject.

10. The method of claim 9 further comprising comparing gait characteristics for a test for the test subject with gait characteristics for the same subject in a previous test, and considering differences in diagnostic determination.

11. The method of claim 10 further comprising a network-connected domain maintaining and updating gait characteristics for a plurality of test subjects, each test subject having a data profile wherein test results are stored chronologically, the network-connected domain executing software on a processor of a server in the domain, providing access to the data to registered practitioners for diagnostic purposes.

12. The method of claim 11 further comprising registration for medical and therapy practitioners, and registration by the registered medical and therapy practitioners of specific test subjects, for which profiles for the specific test subjects are created and maintained, including history of tests.

13. The method of claim 12 further comprising scheduling tests by registered practitioners, and communicating information regarding scheduled tests to test subjects for whom the tests are scheduled.

14. The method of claim 8 comprising arranging the first plurality of pressure sensors in an areal fashion relative to the sole of the first article of footwear, and arranging the second plurality of sensors in an areal fashion relative to the sole of the second article of footwear, providing pressure distribution readings from the sensors relative to time.

\* \* \* \* \*